(12) United States Patent
Stokbroekx et al.

(10) Patent No.: US 7,208,503 B2
(45) Date of Patent: Apr. 24, 2007

(54) ANGIOGENESIS INHIBITING 5-SUBSTITUTED-1,2,4-THIADIAZOLYL DERIVATIVES

(75) Inventors: Raymond Antoine Stokbroekx, Beerse (BE); Marc André Ceusters, Diest (BE); Marcel Jozef Maria Van der Aa, Turnhout (BE); Marcel Gerebernus Maria Luyckx, Geel (BE); Marc Willems, Vosselaar (BE); Robert W. Tuman, Chalfont, PA (US)

(73) Assignee: Janssen Pharmaceutica N.V. (BE)

( * ) Notice: Subject to any disclaimer, the term of this patent is extended or adjusted under 35 U.S.C. 154(b) by 282 days.

(21) Appl. No.: 10/387,703

(22) Filed: Mar. 13, 2003

(65) Prior Publication Data

US 2003/0181460 A1 Sep. 25, 2003

Related U.S. Application Data

(60) Division of application No. 09/998,975, filed on Oct. 19, 2001, now Pat. No. 6,833,369, which is a continuation of application No. 09/446,591, filed on Apr. 21, 2000, now abandoned.

(51) Int. Cl.
*A01N 43/40* (2006.01)
*A61K 31/445* (2006.01)
*C07D 211/68* (2006.01)

(52) U.S. Cl. ..................... 514/318; 546/194
(58) Field of Classification Search ............... 514/318, 514/326, 252.11, 254.04, 252.19, 253.1, 255.05, 514/256; 546/193, 209, 194; 544/295, 357, 544/360, 367, 405
See application file for complete search history.

(56) References Cited

U.S. PATENT DOCUMENTS 5,104,889 A 4/1992 Kanai et al.
6,232,290 B1 * 5/2001 Ohki et al. .................. 514/11

FOREIGN PATENT DOCUMENTS

WO WO 97/26258 A1 7/1997
WO 99-40108 * 8/1999

OTHER PUBLICATIONS

Higgins, R.D. et. al., "Squalamine Improves Retinal Neovascularization." Invest. Oph. & Vis. Sci., May 2000, vol. 41, No. 6, pp. 1507-1512.*
PCT International Search Report dated Oct. 2, 1998 for PCT Appln. No. PCT/EP 98/04022 which relates to U.S. Appl. No. 10/387,703.
Auerbach, R. et al. Assays for Angiogeneis: A Review. *Pharmac. Ther.* 1991 51:1-11.
Blackwell K. et al. Tamoxifen Inhibits Angiogenesis in Estrogen Receptor-Negative Animal Models. *Clin. Cancer Res.* 2000 6(11):4359-4364 at 4359.

Brem S. Angiogenesis and Cancer Control: From Concept to Therapeutic Trial. *Cancer Control, Journal of the Moffitt Cancer Center* 1999, vol. 6, No. 5, 1-32.
Fidler I et al. The Implications of Angiogenesis for the Biology and Therapy of Cancer Metastasis. *Cell* 1994 79: 185-188.
Folkman J et al. Angiogenesis Inhibition and Tumor Regression Caused by Heparin or a Heparin Fragment in the Presence of Cortisone. *Science* 1983 221: 719-725.
Folkman J et al. Clinical Applications of Research on Angiogenesis. *New Eng. J. Med.* 1995 333: 1757-1763.
Folkman J. Klagsbrun M. Angiogenic Factors. *Science.* 1987 235:442-447.
Folkman J. Tumor Angiogenesis: Therapeutic Implications. *N Engl J Med.* 1971 285:1182-1186.
Folkman J. What is the Evidence that Tumors are Angiogenesis Dependent? *J Natl Cancer Inst.* 1990; 82:4-6.

(Continued)

*Primary Examiner*—James O. Wilson
*Assistant Examiner*—Tamthom N. Truong

(57) ABSTRACT

This invention concerns compounds of formula (I)

the N-oxide forms, the pharmaceutically acceptable acid addition salts and stereochemically isomeric forms thereof, wherein X is CH or N; $R^1$ is hydrogen, $C_{1-6}$alkyl, $C_{1-6}$alkyloxy, $C_{1-6}$alkylthio, amino, mono- or di($C_{1-6}$alkyl)amino, $Ar^1$, $Ar^1NH—$, $C_{3-6}$cycloalkyl, hydroxymethyl or benzoyloxymethyl; $R^2$ is hydrogen, $C_{1-6}$alkyl, amino, aminocarbonyl, mono- or di($C_{1-6}$alkyl)amino, $C_{1-6}$alkyloxycarbonyl, $C_{1-6}$alkylcarbonylamino, hydroxy or $C_{1-6}$alkyloxy; $R^3$, $R^4$ and $R^5$ are each independently selected from hydrogen, halo, $C_{1-6}$alkyl, $C_{1-6}$alkyloxy, trifluoromethyl, nitro, amino, cyano, azido, $C_{1-6}$alkyloxy$C_{1-6}$alkyl, $C_{1-6}$alkylthio, $C_{1-6}$alkyloxycarbonyl or $Het^1$;

—(A)— is $Ar^2$, $Ar^2CH_2—$ or $Het^2$; $Ar^1$ and $Ar^2$ optionally substituted phenyl; $Het^1$ and $Het^2$ are optionally substituted monocyclic heterocycles; having angiogenesis inhibiting activity; their preparation, compositions containing them and their use as a medicine.

4 Claims, No Drawings

OTHER PUBLICATIONS

Kim K. et al. Inhibition of Vascular Endothelial Growth Factor-Induced Angiogenesis Suppresses Tumour Growth In Vivo. *Nature* 1993 362:841-844.

Kruger E. A. et al. Endostatin Inhibits Microvessel Formation in the Ex Vivo Rato Aortic Ring Angiogenesis Assay. *BBRC* 2000 268: 183-191.

Kudelka A. et al. Complete Remission of Metastatic Cervical cancer with the Angiogenesis Inhibitor TNP-470 *New Eng. J. Med.* 1998 338:991-992.

Kumar S et al. Psoriasis, Angiogenesis and Hyaluronic Acid. *Laboratory Investigation* 1990 62: 664-665.

Li V. W. et al. Cyclosporine and Angiogenesis in Psoriasis. *J. Am. Acad. Derm.* 1996 35(6):1019-1020.

Liotta L. et al. Cancer Metastasis and Angiogenesis: An Imbalance of Positive and Negative Regulation. *Cell* 1991 64: 327-336.

Lissbrant I et al. Vascular Density Is a Predictor of Cancer-Specific survival in Prostatic Carcinoma. *The Prostate* 1997 33: 38-45.

Lloyd P et al. Vascular Endothelial Growth Factor in Ocular Fluid of Patients With Diabetic Retinopathy and Other Retinal Disorders. *New. Eng. J. Med.* 1994 331: 1480-1487.

Los M et al. The Potential Role of Antivascular Therapy in the Adjuvant and Neoadjuvant Treatment of Cancer. *Semin Oncol* 2001 28:93-105.

Millauer B. et al. Glioblastoma Growth Inhibited In Vivo by a Dominant-Negative Flk-1 Mutant. *Nature* 1994 367: 576-579.

Moses M et al. Inhibitors of Angiogenesis. *Bio/technology* 1991 9: 630-634.

Murray, Clifford J., Editor, *Angiogenesis Protocols*, Human Press, Totowa, NJ 2001 Ch. 13, pp. 185-204.

Nicossia R. F. et al. Endogeneous Regulation of Angiogenesis in the Rat Aorta Model. *Am. J. Pathology* 1997 151(5):1379-1386.

Nissanov, J et al. Methods in Laboratory Investigation: Automatic Vessel Segmentation and Quantification of the Rat Aortic Ring Assay of Angiogenesis. *Lab. Investig.* 1995 73: 734-739.

O'Reilly M et al. Angiostatin: A Novel Angiogenesis Inhibitor That Mediate the Suppression of Metastases by a Lewis Lung Carcinoma. *Cell* 1994 79: 315-328.

O'Reilly M et al. Endostatin: An Endogenous Inhibitor of Angiogenesis and Tumor Growth. *Cell* 1997 88: 277-285.

Perez-Atayde A. et al. Spectrum of Tumor Angiogenesis in the Bone Marrow of Children with Acute-Lymphoblastic Leukemia. *Am. J. Pathology* 1997 150-815-820.

Plate K. et al. Vascular Endothelial Growth Factor is a Potential Tumour Angiogenesis Factor in Human Gliomas In vivo. *Nature* 1992 359:845-848.

Shweiki D et al. Vascular Endothelial Growth Factor Induced by Hypoxia May Mediate Hypoxia-Initiated Angiogenesis. *Nature* 1992 359: 843-845.

Singh R. et al. Interferons $\alpha$ and $\beta$ Down-Regulate the Expression of Basic Fibroblast Growth Factor in Human Carcinomas. *Proc. Natl. Acad. Sci.* 1995 92: 4562-4566.

Teicher B.A. et al. Antiangiogenic Agents Potentiate Cytoxic Cancer Therapies Against Primary and Metastatic Disease. *Cancer Research* 1992 52: 6702-6704.

Watson S. et al. Inhibition of Organ Invasion by the Matrix Metalloproteinase Inhibitor Batimastat (BB-94) in Two Human Colon Carcinoma Metastasis Models. *Cancer Research* 1995 55: 3629-3633.

Weidner N et al. Tumor Angiogenesis and Metastasis—Correlation in Invasive Breast Carcinoma *New. Eng. J. Med.* 1991 324: 1-8.

Wolf J. Angiogenesis in Normal and Psoriatic Skin. *Laboratory Investigation* 1989 61: 139-142.

\* cited by examiner

ANGIOGENESIS INHIBITING 5-SUBSTITUTED-1,2,4-THIADIAZOLYL DERIVATIVES

CROSS REFERENCE TO RELATED APPLICATIONS

This application is a divisional application of the application Ser. No. 09/998,975, filed Oct. 19, 2001 now U.S. Pat. No. 6,833,369, which application is a continuation of the application Ser. No. 09/446,591 filed Apr. 21, 2000 now abandoned, which application claims priority from EP 97201931.9, filed Jun. 24, 1997 and US provisional application No. 60/053,003, filed Jul. 10, 1997.

This invention concerns 5-substituted-1,2,4-thiadiazolyl derivatives acting as angiogenesis inhibitors, and their preparation; it further relates to compositions comprising them, as well as their use as a medicine.

Angiogenesis, i.e. the formation of new vessels by endothelial cells, plays an important role in a variety of physiologic and pathophysiologic processes. The development of a vascular supply is essential for the growth, maturation and maintenance of normal tissues. It is also required for wound healing. Angiogenesis is critical for solid tumor growth and metastasis and is involved in a variety of other pathological conditions such as neovascular glaucoma, diabetic retinopathy, psoriasis and rheumatoid arthritis. These pathological states are characterized by augmented angiogenesis during which normally quiescent endothelial cells become activated, degrade extracellular matrix barriers, proliferate, and migrate to form new vessels. To control these angiogenesis dependent disorders, compounds with angiogenesis inhibitory properties would be very useful.

Several compounds inhibiting angiogenesis, also called angiostatics, angio-inhibitors or angiogenic antagonists, are disclosed in the art. For instance hydrocortisone is a well known angiogenesis inhibitor (Folkman et al., Science 230: 1375, 1985' "A new class of steroids inhibits angiogenesis in the presence of heparin or a heparin fragment"; Folkman et al., Science 221:719, 1983, "Angiogenesis inhibition and tumor regression caused by heparin or a heparin fragment in the presence of cortisone").

EP-0,398,427, published on Nov. 22, 1990, discloses antirhinoviral pyridazinames, and in EP-0,435,381, published on Jul. 3, 1991, pyridazinamines are described having antipicornaviral activity. EP-0,429,344, published on May 29, 1991, discloses aminopyridazine derivatives as cholinergic agonists.

The compounds of the present invention differ from the prior art compounds by the fact that they are invariably substituted with a thiadiazolyl moiety and particularly by the fact that unexpectedly these compounds have angiogenesis inhibiting properties.

This invention concerns compounds of formula

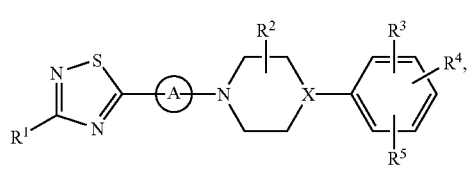

(I)

the N-oxide forms, the pharmaceutically acceptable acid addition salts and stereochemically isomeric forms thereof, wherein X is CH or N;

$R^1$ is hydrogen, $C_{1-6}$alkyl, $C_{1-6}$alkyloxy, $C_{1-6}$alkylthio, amino, mono- or di($C_{1-6}$alkyl)amino, $Ar^1$, $Ar^1NH-$, $C_{3-6}$cycloalkyl, hydroxymethyl or benzyloxymethyl;

$R^2$ is hydrogen, $C_{1-6}$alkyl, amino, aminocarbonyl, mono- or di($C_{1-6}$alkyl)amino, $C_{1-6}$alkyloxycarbonyl, $C_{1-6}$alkylcarbonylamino, hydroxy or $C_{1-6}$alkyloxy;

$R^3$, $R^4$ and $R^5$ are each independently selected from hydrogen, halo, $C_{1-6}$alkyl, $C_{1-6}$alkyloxy, trifluoromethyl, nitro, amino, cyano, azido, $C_{1-6}$alkyloxy$C_{1-6}$alkyl, $C_{1-6}$alkylthio, $C_{1-6}$alkyloxycarbonyl or $Het^1$;

is $Ar^2$, $Ar^2CH_2-$ or $Het^2$;

$Ar^1$ is phenyl; phenyl substituted with 1, 2 or 3 substituents each independently selected from halo, $C_{1-6}$alkyl, $C_{1-6}$alkyloxy, trihalomethyl, amino or nitro;

$Ar^2$ is phenyl; phenyl substituted with 1, 2 or 3 substituents each independently selected from halo, $C_{1-6}$alkyl, $C_{1-6}$alkyloxy, trihalomethyl, amino or nitro;

$Het^1$ is a monocyclic heterocycle selected from oxazolyl, isoxazolyl, oxadiazolyl, thiazolyl, isothiazolyl, thiadiazolyl or oxazolinyl; and each monocyclic heterocycle may optionally be substituted on a carbon atom with $C_{1-4}$alkyl; and $Het^2$ is a monocyclic heterocycle selected from furanyl, thiofuranyl, oxadiazolyl, thiadiazolyl, pyridinyl, pyrimidinyl or pyrazinyl; and each monocyclic heterocycle may optionally be substituted on a carbon atom with 1 or 2 substituents each independently selected from halo, $C_{1-4}$alkyl, $C_{1-4}$alkyloxy, nitro or trifluoromethyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; $C_{1-6}$alkyl is meant to include $C_{1-4}$alkyl and the higher homologues thereof having 5 to 6 carbon atoms such as, for example, pentyl, 2-methylbutyl, hexyl, 2-methylpentyl and the like.

Examples of the

moiety are

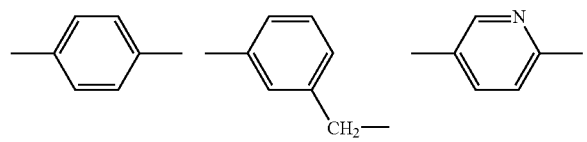

-continued

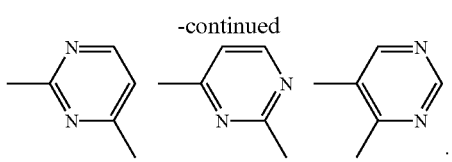

Wherever

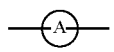

is a radical of formula Ar²CH₂, the CH₂ moiety of said radical preferably is connected to the nitrogen atom of the piperidinyl moiety when X is CH, or piperazinyl moiety when X is nitrogen.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

Whenever used hereinafter, the term "compounds of formula (I)" is meant to include also the pharmaceutically acceptable acid addition salts and all stereoisomeric forms.

A group of interesting compounds consists of those compounds of formula (I) wherein one or more of the following restrictions apply:

a) X is N;
b) R¹ is hydrogen, C₁₋₆alkyl, amino or di(C₁₋₆alkyl)amino;
c) R² is hydrogen;
d) R³, R⁴ and R⁵ are each independently selected from hydrogen, halo, C₁₋₆alkyl, C₁₋₆alkyloxy, trifluoromethyl, nitro or C₁₋₆alkyloxycarbonyl.

A particular group of compounds are those compounds of formula (I) wherein X is N; R¹ is hydrogen, C₁₋₄alkyl or di(C₁₋₄alkyl)amino; R² is hydrogen; R³, R⁴ and R⁵ are each independently selected from hydrogen, halo, C₁₋₄alkyl, C₁₋₄alkyloxy or trifluoromethyl; and the bivalent radical

is Ar², Ar²CH₂— or Het² wherein Ar² is phenyl, or phenyl substituted with 1 or 2 substituents each independently selected from halo, C₁₋₆alkyl, C₁₋₆alkyloxy, trihalomethyl, amino or nitro; and Het² is thiadiazolyl, pyridinyl, pyrimidinyl or pyrazinyl.

A preferred group of compounds are those compounds of formula (I) wherein X is N, R¹ is methyl, R² is hydrogen, R³ and R⁴ are hydrogen and R⁵ is trifluoromethyl.

A more preferred group of compounds are those preferred compounds wherein R⁵ is trifluoromethyl situated on the 3-position.

Most preferred are:
1-[4-(3-methyl-1,2,4-thiadiazol-5-yl)phenyl]-4-[3-(trifluoromethyl)phenyl]piperazine, and
1-[5-(3-methyl-1,2,4-thiadiazol-5-yl)-2-pyridinyl]-4-[3-(trifluoromethyl)-phenyl]-piperazine, and the pharmaceutically acceptable acid addition salts, the stereoisomeric forms, or the N-oxides thereof.

The compounds of the present invention can generally be prepared by reacting an intermediate of formula (II) with an intermediate of formula (III).

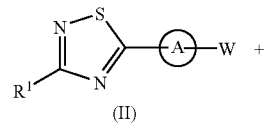

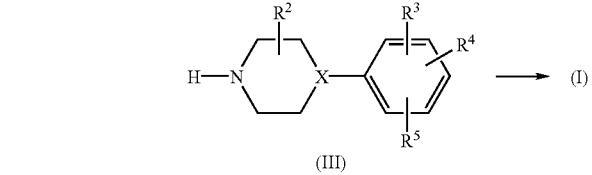

In the foregoing and following reaction schemes W represents an appropriate reactive leaving group such as, for example, halo, e.g. fluoro, chloro, bromo, iodo, or in some instances W may also be a sulfonyloxy group, e.g. methanesulfonyloxy, benzene-sulfonyloxy, trifluoromethanesulfonyloxy and the like reactive leaving groups. Said reaction is performed following art-known procedures such as for instance stirring both reactants together in a reaction-inert solvent, e.g. N,N-dimethylformamide, acetonitrile, methyl isobutylketone and the like, preferably in the presence of a base, e.g. sodium hydrogen carbonate, sodiumcarbonate or triethylamine. The reaction may conveniently be carried out at a temperature ranging between room temperature and the reflux temperature of the reaction mixture.

The compounds of formula (I) wherein $R^1$ is $CH_3$, said compounds being represented by formula (I-a) can also be prepared by treating an intermediate of formula (IV) with hydroxylamino-O-sulfonic acid in a reaction-inert solvent such as, e.g. methanol or ethanol, in the presence of a base such as, e.g. pyridine.

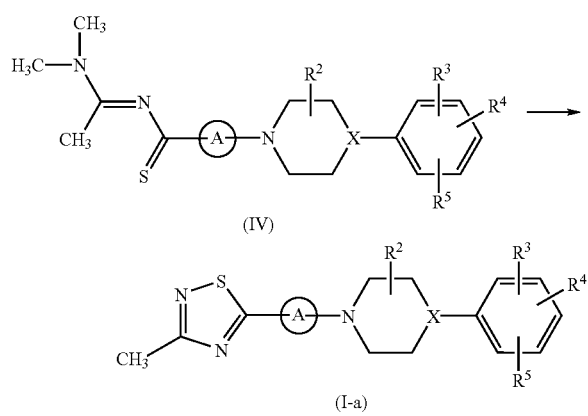

The compounds of formula (I) may further be prepared by converting compounds of formula (I) into each other according to art-known group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For instance, some intermediates of formula (II), such as 5-(4-fluorophenyl)-3-methyl-1,2,4-thiadiazole, have been described by Yang-i Lin et al. in *J. Org. Chem.*, 45(19), p. 3750–3753 (1980), and some intermediates of formula (III), such as 1-[3-(trifluoromethyl)phenyl]-piperazine, are commercially available.

Intermediates of formula (II) may be prepared by reacting compounds of formula (V), wherein W is an appropriate leaving group as defined above, with an intermediate of formula (VI), optionally added as its acid addition salt.

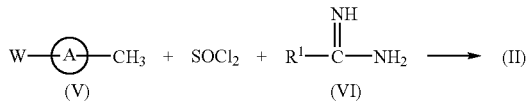

Intermediates of formula (IV) can be prepared as outlined in scheme I.

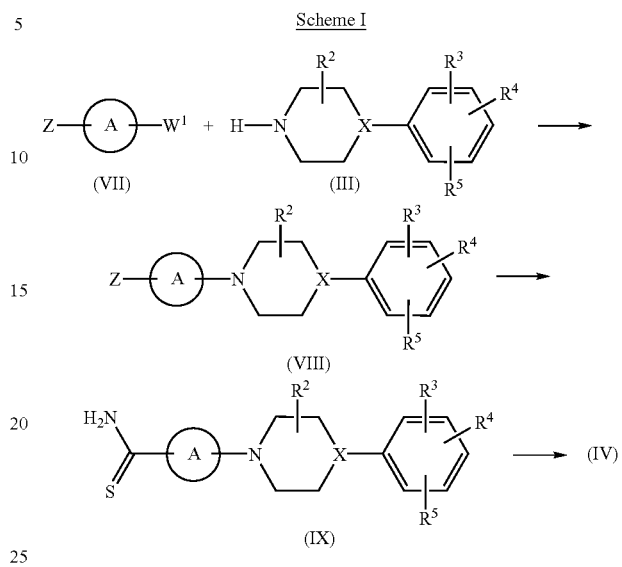

In scheme I, an intermediate of formula (VII), wherein $W^1$ is an appropriate leaving group such as halo or sulfonyloxy and Z is cyano or aminocarbonyl, is reacted with an intermediate of formula (III) under art-known reaction procedures as described hereinabove for the synthesis of compounds of formula (I). The resulting intermediates of formula (VIII) are treated with Lawesson's reagent in a suitable solvent such as, for example, toluene or pyridine, or are treated with $H_2S$ in a suitable solvent such as, e.g. N,N-dimethylformamide, optionally in the presence of triethylamine. Subsequently, intermediates of formula (IX) are treated with N,N-dimethylacetamide dimethyl acetal in a reaction-inert solvent such as, e.g. toluene or dichloromethane, thereby yielding intermediates of formula (IV).

Compounds of formula (I) and some of the intermediates may have one or more stereogenic centers in their structure, present in a R or a S configuration. For instance, $R^1$, $R^2$, $R^3$, $R^4$ or $R^5$ can be a $C_{1-6}$alkyl having a stereogenic center.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Suitable chiral stationary phases are, for example, polysaccharides, in particular cellulose or amylose derivatives. Commercially available polysaccharide based chiral stationary phases are ChiralCel CA, OA, OB, OC, OD, OF, OG, OJ and OK, and Chiralpak AD, AS, OP(+) and OT(+). Appropriate eluents or mobile phases for use in combination with said polysaccharide chiral stationary phases are hexane and the like, modified with an alcohol such as ethanol, isopropanol and the like. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) have valuable pharmacological properties in that they inhibit angiogenesis, both in vivo and in vitro.

In view of their pharmacological activity, the compounds of formula (I), their pharmaceutically acceptable acid addition salts, stereochemically isomeric forms, or N-oxide forms thereof, are inhibitors of angiogenesis. Therefore, angiogenesis inhibitors are useful to control or treat angiogenesis dependent disorders such as, e.g. ocular neovascular diseases, neovascular glaucoma, diabetic retinopathy, retrolental fibroplasia, hemangiomas, angiofibromas, psoriasis, osteoarthritis and rheumatoid arthritis. Also, angiogenesis inhibitors are useful to control solid tumor growth, such as, e.g. breast, prostate, melanoma, renal, colon, cervical cancer and the like; and metastasis.

Hence, the present invention discloses the compounds of formula (I) for use as a medicine as well as the use of these compounds of formula (I) for the manufacture of a medicament for treating angiogenesis dependent disorders.

In view of the usefulness of the subject compounds in the treatment or prevention of angiogenesis dependent disorders, the present invention provides a method of treating warm-blooded animals suffering from such disorders, said method comprising the systemic administration of a therapeutic effective amount of a compound of formula (I), a N-oxide or a pharmaceutically acceptable acid addition salt thereof.

In view of their useful pharmacological properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermnal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxy-propyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection. conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

Those skilled in the art could easily determine the effective amount from the test results presented hereinafter. In general it is contemplated that an effective amount would be from 0.001 mg/kg to 10 mg/kg body weight, and in particular from 0.01 mg/kg to 1 mg/kg body weight. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

The following examples are provided for purposes of illustration

Experimental Part

Hereinafter "DMF" means N,N-dimethylformamide, "DCM" means dichloromethane, "DIPE" means diisopropylether and "THF" means tetrahydrofuran.

A. Preparation of the Intermediates

EXAMPLE A.1 a) A mixture of 2-chloro-4-methylpyrimidinyl (0.07 mol) in thionyl chloride (100 ml) was stirred and refluxed for 16 hours. The solvent was evaporated yielding 2-chloro-4-[dichloro(chlorothio)methyl]pyrimidine (intermediate 1).
b) 1-Imino-ethanamine hydrochloride (1:1) (0.08 mol) was added at 0° C. to a stirring mixture of intermediate 1 (0.07 mol) in DCM (300 ml). Sodium hydroxide (50%, 20 ml) was added dropwise at 0° C. The mixture was stirred at 5° C. for 1 hour. Water (300 ml) and DCM (300 ml) were added. The mixture was separated into its layers. The aqueous layer was washed twice with DCM. The combined organic layer was dried, filtered and the solvent was evaporated. The residue was purified over silica gel on a glass filter (eluent:DCM). Two pure fractions were collected and their solvents were evaporated, yielding 3.5g of 2-chloro-4-(3-methyl-1,2,4-thiadiazol-5-yl)pyrimidine (intermediate 2).

EXAMPLE A.2 a) A mixture of 6-chloro-3-pyridinecarboxamide (0.11 mol), 1-[3-(trifluoromethyl)-phenyl]-piperazine (0.11 mol) and sodium carbonate (0.22 mol) in DMF (300 ml) was stirred at 120° C. overnight. The mixture was poured out into ice water (600 ml) and stirred for 1 hour. The precipitate was filtered off and dried Part of this fraction (4 g) was taken up in DCM and an aqueous $NaHCO_3$ solution. The mixture was separated into its layers. The aqueous layer was extracted three times with DCM. The combined organic layer was dried, filtered and the solvent was evaporated till a small volume. The precipitate was filtered off and dried, yielding 3.2 g of 6-[4-[3-(trifluoromethyl)phenyl]-1-piperazinyl]-3-pyridinecarboxamide (intermediate 3).
b) A mixture of intermediate 3 (0.013 mol) and Lawesson's reagens (0.007 mol) in toluene (130 ml) was stirred and refluxed for 2 hours. The mixture was cooled. Water (100 ml) was added. The mixture was stirred for 1 hour and separated into its layers. The aqueous layer was extracted three times with toluene and once with DCM. The combined organic layer was dried, filtered and the solvent was evaporated, yielding: 7.3g of 6-[4-[3-(trifluoromethyl)phenyl]-1-piperazinyl]-3-pyridinecarbothioamide (intermediate 4).

EXAMPLE A.3

A mixture of intermediate 4 (0.013 mol) and 1,1-dimethoxy-N,N-dimethyl-ethanamine (0.021 mol) was allowed to stand overnight and then used without further purification, yielding N-[1-(dimethylamino)ethylidene]-6-[4-[3-(trifluoromethyl)phenyl]-1-piperazinyl]-3-pyridinecarbothioamide (intermediate 5). Table 1.1 lists the intermediates that were prepared according to example A.3.

TABLE I.1

| Intm. No. | Ex. No. | Structure | Physical data |
|---|---|---|---|
| 5 | A.3 | 6-methyl-pyridin-3-yl thioamide with N,N-dimethyl amidine | — |
| 6 | A.3 | 3-methyl-pyrazin-2-yl thioamide with N,N-dimethyl amidine | mp. 156° C. |
| 7 | A.3 | 2-methylphenyl thioamide with N,N-dimethyl amidine | — |
| 8 | A.3 | 3-methylphenyl thioamide with N,N-dimethyl amidine | — |
| 9 | A.3 | 2-methyl-pyridin-3-yl thioamide with N,N-dimethyl amidine | — |

TABLE I.1-continued

| Intm. No. | Ex. No. | Structure | Physical data |
|---|---|---|---|
| 10 | A.3 | 3-(CH₂—) methylphenyl thioamide with N,N-dimethyl amidine | — |

B. Preparation of the Final Compounds

EXAMPLE B.1

A mixture of 5-(4-fluorophenyl)-3-methyl-1,2,4-thiadiazole (0.012 mol), 1-[3-(trifluoromethyl)phenyl]-piperazine (0.014 mol) and sodium carbonate (0.024 mol) in DMF (10 ml) was stirred at 140° C. for 24 hours, then at 150° C. for 24 hours, cooled, poured out into ice water (200 ml) and stirred. The precipitate was filtered off, taken up in DCM, dried, filtered and the solvent was evaporated. The residue was crystallized from DIPE. The precipitate was filtered off and dried, yielding 2.5g (52%) of 1-[4-(3-methyl-1,2,4-thiadiazol-5-yl)phenyl]-4-[3-(trifluoromethyl)phenyl]piperazine (compound 2).

EXAMPLE B.2

A mixture of hydroxylamine-O-sulfonic acid (0.011 mol) in methanol (15 ml) was added at once to a mixture of intermediate 5 (0.01 mol) and pyridine (0.02 mol) in ethanol (40 ml). The mixture was stirred at room temperature for 90 minutes. The solvent was evaporated. The residue was dissolved in DCM, washed with water and an aqueous NaOH 0.1N solution, dried, filtered and the solvent was evaporated. The residue was taken up in methanol, filtered off and dried. The residue was taken up in acetonitrile (100 ml). The mixture was stirred and boiled until complete dissolution and then allowed to crystallize out. The precipitate was filtered off and dried, yielding 1.4 g (35%) of 1-[5-(3-methyl-1,2,4-thiadiazol-5-yl)-2-pyridinyl]-4-[3-(trifluoromethyl)-phenyl]-piperazine (compound 6).

Table F.1 lists the compounds that were prepared according to one of the above examples and table F.2 lists both the experimental (column heading "exp.") and theroretical (column heading "theor.") elemental analysis values for carbon, hydrogen and nitrogen of the compounds as prepared in the experimental part hereinabove.

TABLE F.1

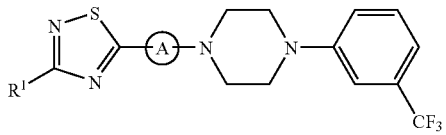

| Co. No. | Ex. No. | R¹ | Physical data |
|---|---|---|---|
| 1 | B.1 | (5-methyl-1,3,4-thiadiazol-2-yl with CH₃) | mp. 184.8° C. |
| 2 | B.1 | (4-methylphenyl with CH₃) | — |
| 3 | B.2 | (2-methylphenyl with CH₃) | — |
| 4 | B.2 | (3-methylphenyl with CH₃) | .HCl (1:1) |
| 5 | B.2 | (3-(CH₂—)phenyl with CH₃) | .HCl (1:1) |
| 6 | B.2 | (6-methylpyridin-3-yl with CH₃) | — |
| 7 | B.2 | (2-methylpyridin-3-yl with CH₃) | — |
| 8 | B.1 | (2-methylpyrimidin-4-yl with CH₃) | — |
| 9 | B.1 | (4-methylpyrimidin-2-yl with CH₃) | mp. 140° C. |

TABLE F.1-continued

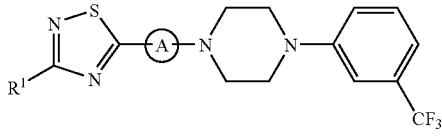

| Co. No. | Ex. No. | R¹ | Physical data |
|---|---|---|---|
| 10 | B.2 | (3-methylpyrazin-2-yl with CH₃) | mp. 140° C. |

TABLE F.2

| Comp. No. | Carbon Exp. | Carbon Theor. | Hydrogen Exp. | Hydrogen Theor. | Nitrogen Exp. | Nitrogen Theor. |
|---|---|---|---|---|---|---|
| 2 | 59.39 | 59.31 | 4.73 | 4.68 | 13.85 | 13.88 |
| 3 | 59.39 | 59.32 | 4.73 | 4.67 | 13.85 | 13.92 |
| 5 | 55.44 | 55.29 | 4.87 | 4.96 | 12.32 | 12.39 |
| 6 | 56.29 | 55.30 | 4.47 | 4.33 | 17.27 | 17.06 |
| 7 | 56.29 | 56.24 | 4.47 | 4.45 | 17.27 | 17.43 |
| 8 | 53.19 | 52.21 | 4.22 | 4.07 | 20.68 | 20.33 |

C. Pharmacological Examples

EXAMPLE C.1

Angiogenesis inhibitory activity was measured in vitro using the rat aortic ring model of angiogenesis as described by Nicosia, R. F. and Ottinetti in "Laboratory Investigation", vol. 63, p. 115, 1990. The ability of compounds to inhibit microvessel formation was compared to vehicle-treated control rings. Quantitation (microvessel area) following eight days in culture was performed using an image analysis system, consisting of a light microscope, a CCD camera and an automated, custom-designed image analysis program as described by Nissanov, J., Tuman, R. W., Gruver, L. M., and Fortunato, J. M. in "Laboratory Investigation", vol 73 (#5), p. 734, 1995. Compounds were tested at several concentrations for determination of inhibitory potency ($IC_{50}$'s). Compounds 1, 2 and 6 have an $IC_{50}$ value lower than 10 nM.

What is claimed is:

1. A compound of formula (I),

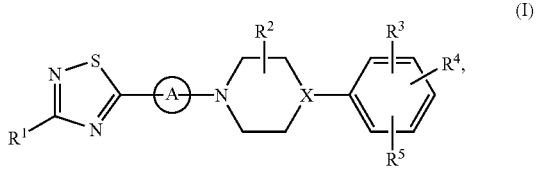

the N-oxide forms, the pharmaceutically acceptable acid addition salts and stereochemically isomeric forms thereof, wherein X is CH;

$R^1$ is hydrogen, $C_{1-6}$alkyl, $C_{1-6}$alkyloxy, $C_{1-6}$alkylthio, amino, mono- or di($C_{1-6}$alkyl)amino, $Ar^1$, $Ar^1NH-$, $C_{3-6}$cycloalkyl, hydroxymethyl or benzyloxymethyl;

$R^2$ is hydrogen, $C_{1-6}$alkyl, amino, aminocarbonyl, mono- or di($C_{1-6}$alkyl)amino, $C_{1-6}$alkyloxycarbonyl, $C_{1-6}$alkylcarbonylamino, hydroxy or $C_{1-6}$alkyloxy;

$R^3$, $R^4$ and $R^5$ are each independently selected from hydrogen, halo, $C_{1-6}$alkyl, $C_{1-6}$alkyloxy, trifluoromethyl, nitro, amino, cyano, azido, $C_{1-6}$alkyloxy$C_{1-6}$alkyl, $C_{1-6}$alkylthio, $C_{1-6}$alkyloxycarbonyl or $Het^1$;

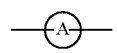

is $Het^2$;

$Ar^1$ is phenyl; phenyl substituted with 1, 2 or 3 substituents each independently selected from halo, $C_{1-6}$alkyl, $C_{1-6}$alkyloxy, trihalomethyl, amino or nitro;

$Het^1$ is a monocyclic heterocycle selected from oxazolyl, isoxazolyl, oxadiazolyl, thiazolyl, isothiazolyl, thiadiazolyl or oxazolinyl; and each monocyclic heterocycle may optionally be substituted on a carbon atom with $C_{1-4}$alkyl; and $Het^2$ is a monocyclic heterocycle selected from pyridinyl; and said monocyclic heterocycle may optionally be substituted on a carbon atom with 1 or 2 substituents each independently selected from halo, $C_{1-4}$alkyl, $C_{1-4}$alkyloxy, nitro or trifluoromethyl.

2. A composition comprising a pharmaceutically acceptable carrier, and as active ingredient a therapeutically effective amount of a compound as claimed in claim 1.

3. A process of preparing a compound as claimed in claim 1, wherein a) an intermediate of formula (II) is reacted with an intermediate of formula (III) in a reaction-inert solvent and, optionally in the presence of a suitable base;

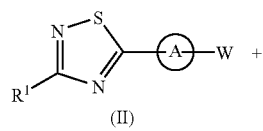
(II)

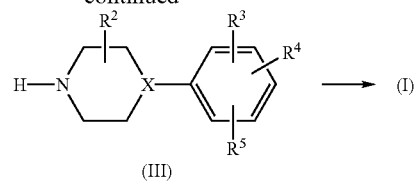
(III)

b) an intermediate of formula (IV) is treated with hydroxylamino-O-sulfonic acid in a reaction-inert solvent, in the presence of a suitable base, thereby yielding compounds of formula (I-a), defined as compounds of formula (I) wherein $R^1$ is methyl;

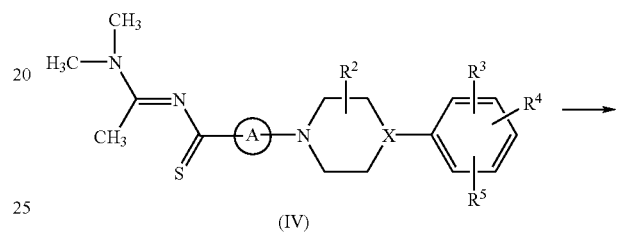
(IV)

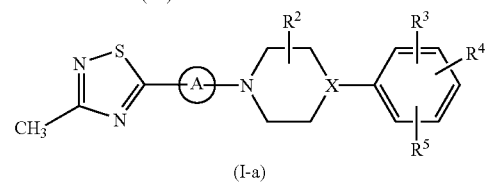
(I-a)

wherein in the above reaction schemes the radicals X, $R^1$, $R^2$, $R^3$, $R^4$, $R^5$ and

are as defined in claim 1, and W is an appropriate leaving group;

c) or, a compound of formula (I) is converted into another compound of formula (I); or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

4. A method of treating angiogenesis dependent disorders selected from the group consisting of ocular neovascular diseases, neovascular glaucoma, and diabetic retinopathy; comprising the step of administering to a host in need thereof an effective amount of a compound of claim 1.

* * * * *